United States Patent [19]

Gottfried

[11] 4,039,039

[45] Aug. 2, 1977

[54] INFLATABLE ANTI-SHOCK AND SPLINTING TROUSERS

[75] Inventor: Max Gottfried, Rossford, Ohio

[73] Assignee: Jobst Institute Inc., Toledo, Ohio

[21] Appl. No.: 662,801

[22] Filed: Mar. 1, 1976

[51] Int. Cl.² .............................................. A61F 5/04
[52] U.S. Cl. .......................... 128/87 R; 128/DIG. 20; 2/DIG. 3
[58] Field of Search .................. 128/89, 87 R, 60, 78, 128/133, 134, DIG. 20, 24 R; 2/DIG. 3

[56] References Cited

U.S. PATENT DOCUMENTS

| | | | |
|---|---|---|---|
| 3,823,711 | 7/1974 | Hatton | 128/78 |
| 3,823,712 | 7/1974 | Morel | 128/87 R |
| 3,933,150 | 1/1976 | Kaplan et al. | 128/24 R |

*Primary Examiner*—John D. Yasko
*Attorney, Agent, or Firm*—David H. Wilson, Jr.

[57] ABSTRACT

Several embodiments of inflatable trousers and their auxiliary equipment are disclosed whereby the trousers are inflated in a controlled and precise manner. The form of the garment facilitates application to an infirmed individual by having a front and rear panel which are integral along the inseam of the legs, are separate at the top of an abdominal region, the region of the perineum and at the bottoms of the legs, and are separable along the outer side margins from the top to the bottoms of the legs. Fasteners such as slide fasteners are provided for selective closure along the outer side margins of the garment. One or more inflatable chambers are located within the garment to extend over substantial regions thereof and impose pressure over the enclosed body portion as the entire enclosed abdominal area and both legs or, selectively, the respective legs and an abdominal region. A relatively rigid outer reinforcing panel militates against ballooning in the abdominal region. Selective valving between the chambers and the exterior of the garment enables gas pressure adjustments within the respective chambers as where treatment requires access to a leg or the lower abdomen. Aneroid gauge couplings and bleed valves either in the pressurizing gas lines or in separate conduits to the chamber interiors facilitate precise adjustment of pressures. Color coding of controls, gauges and conduits and/or their couplings facilitate utilization of polychambered garments.

16 Claims, 7 Drawing Figures

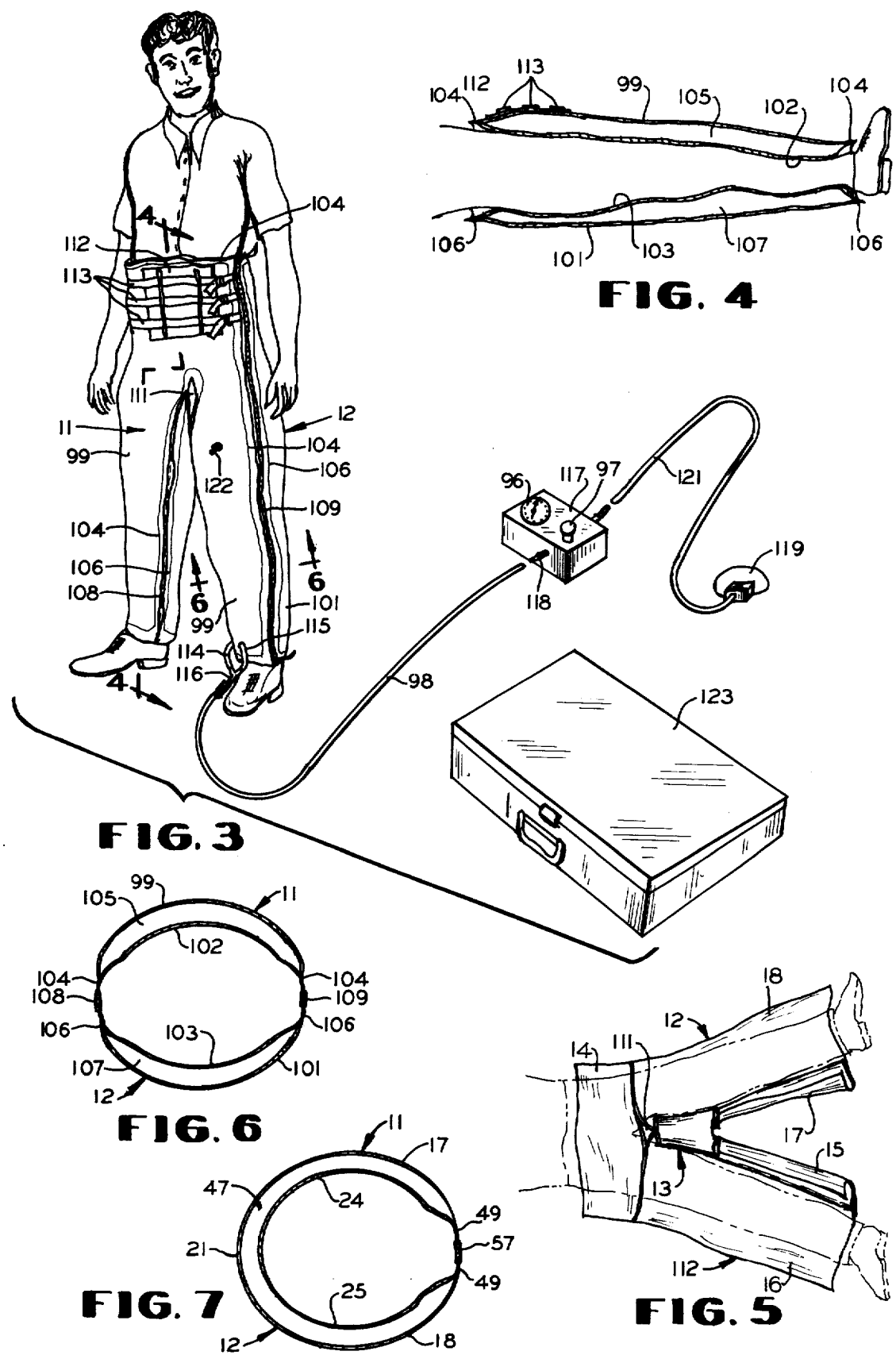

INFLATABLE ANTI-SHOCK AND SPLINTING TROUSERS

BACKGROUND OF THE INVENTION

1. Field of the Invention

This invention relates to inflatable garments particularly such as are used for first aid or emergency use on patients either inside or outside of a hospital. It is adapted for rapid application at the site of an accident to immobilize the body below the rib cage, impose pressure to reduce or inhibit bleeding and to displace blood flow to the lower torse and legs thereby raising blood pressure and functioning as an instant auto transfusion of that blood to the brain and other vital organs.

2. Description of the Prior Art

Heretofore the application of inflatable appliances to the lower torso for the treatment of shock, bleeding and to immobilize the patient has been proposed as in Gardner U.S. Pat. No. 3,460,531 of Aug. 12, 1969, for "Inflatable Spling With Lacing Means." More recenty, Pat. 3,933,150 to Kaplan et al. for a "Medical Pneumatic Trouser for Emergency Autotransfusion" disclosed another form of inflatable garment for these purposes. In the case of the Gardner tubular splint it merely encases the entire lower torso without affording any perineal relief or any access to individual legs or the abdominal region of the patient. The trousers of Kaplan et al. are applied as a wrap around appliance and are prone to become released in the overlapping areas of inflation, particularly where Velcro type fasteners are employed. They also present lengths of leg material on each side of a patient placed upon the trousers so that it is awkward to properly place the respective portions of the leg wrapping only partially across the patient's leg and obtain a smooth and comfortable fit, or an effective unifrom closure along the length of the legs. Other inflatable splinting and pressurizing appliances are knwon such as the double walled tubular splints of Jobst U.S. Pat. No. 2,747,570, Gottfried U.S. Pat. Nos. 3,083,708 and 3,153,413 and Brown U.S. Pat. No. 2,694,395, however these appliances were not concerned with convenience of application to enclose the individual legs and abdomen of a patient.

SUMMARY OF THE INVENTION

The present anti-shock trousers comprise a conveniently applied inflatable garment which imposes pressure over the lower body regions while affording access to the patient for localized treatment. It involves an outer cover of flexible sheet material which can be wall of a gas chamber and in some instances is as impervious. The cover is comprised of front and rear sections joined along the inseam portions of the legs so that a patient can be placed on the lower or back section with the leg and abdominal regions of the front positioned to be drawn between the patient's legs, laid across the patient and joined at the other side margins with the corresponding margins of the rear section. An abdominal panel inhibits ballooning of the garment in that region when its belts are cinched to snugly fit the patient. Gas chambers within the garment are then inflated to impose a pressure on the enclosed body portions of the patient.

BRIEF DESCRIPTION OF THE DRAWINGS

FIG. 3 is a perspective view of another form of the garment shown applied to a patient and inflated and having front and rear inflatable chambers and a simplified accessory system for inflation and pressure control;

FIG. 4 is a simplified longitudinal side view, taken in section along the line 4—4 of FIG. 3, of the garment of FIG. 3 in inflated condition and applied to a prone patient;

FIG. 5 is a perspective view of the garment prepared to be applied to a patient by folding the upper or front section into the area between that to be occupied by the patient's legs so it can be drawn through the legs and spread over the patient;

FIG. 6 is a cross-sectional view on the left leg of the trousers with the garment inflated to impose pressure on the leg as shown in FIG. 3, taken along the line 6—6 of FIG. 3; and FIG. 7 is a cross-section corresponding to FIG. 6 of an inflated trouser leg of the garment of FIG. 1.

DETAILED DESCRIPTION OF THE PREFERRED EMBODIMENT

Figure 1:
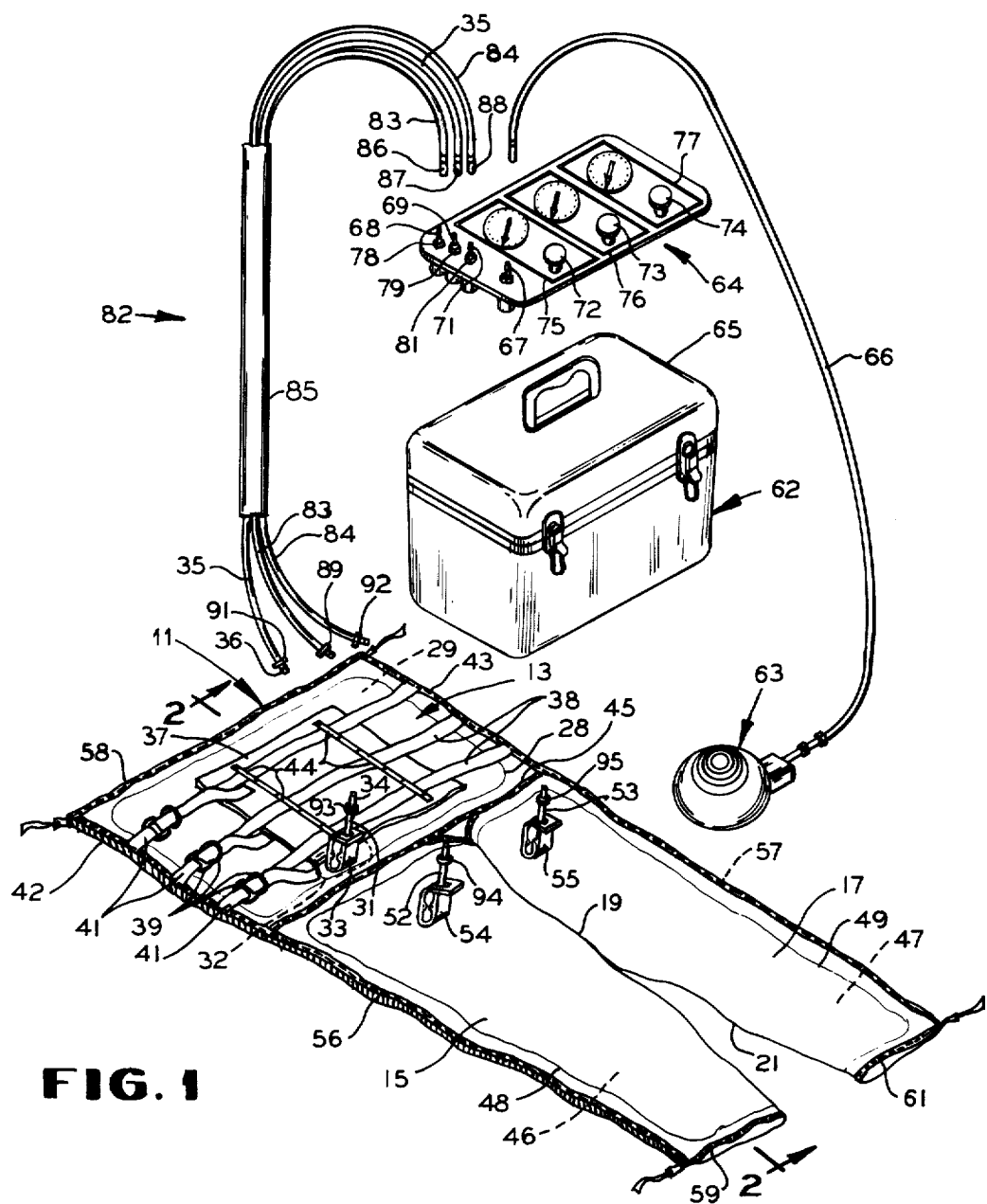
FIG. 1 is a perspective view of one form of the garment having three separately inflatable chambers with certain elements separated and presented in exploded view portaryal to facilitate illustration of an emergency kit form of its utilization.
Figure 2:
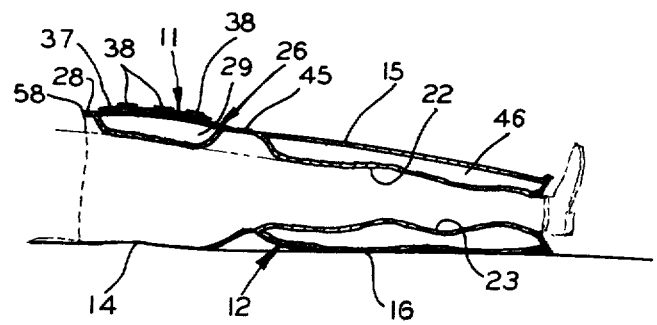
FIG. 2 is a simplified longitudinal side view taken in section along line 2—2 of FIG. 1, of the garment of FIG. 1, applied to a patient and inflated.

The two embodiments of the anti-shock trousers of this invention have a generally common outline geometry which, as shown in FIGS. 1, 2 and 7 comprises front and rear panels 11 and 12 including a front abdominal panel 13 and a rear abdominal panel 14. Front and rear right and left leg outer panels 15, 16, 17 and 18 depend from the respective front and rear abdominal panels and are joined along the inseam regions of each leg as at 19 and 21.

Inner leg panels for the front and rear of the right and left legs 22, 23, 24 and 25 are integral with the inner abdominal panel for the front 26 and the rear abdominal panel 14 respectively. In practice, the inner and outer panels are of a flexible material which is impervious to gas and they are sealed together along marginal regions to form chambers which can be inflated. The outer side margins in the major planes of the front and rear panels 11 and 12 are separate so that the trousers can be opened along their length on both sides. This geometry enables the trousers to be applied to a patient by placing the rear panel 12 on a supporting surface such as a stretcher or blanket and to be folded as shown in FIG. 5 so that the front panel leg portions lie along the inseam region of each leg and the front abdominal panel 13 is folded downward or gathered in the crotch region of the trousers. A patient can be placed on the rear panel 12 and the front panel drawn between his legs and acorss the top of his legs and lower abdomen.

In the form of the garment shown in FIGS. 1, 2 and 7 four sections are employed. The abdominal region is made of separate front and back subassemblies and each leg is a subassembly and inflatable chambers are provided in the front abdominal section and in each leg section. A generally rectangular panel of a double layer of a suitable gas impervious fabric such as neoprene impregnated nylon or polyurathane impregnated nylon is formed by sealing the panels 13 and 26 together around their marginal regions as by cementing them along a marginal band 28, in the case of neoprene impregnated nylon, or by heat sealing them along the band 28, in the case of polyurathene impregnated nylon. The chamber 29 within the band 28 is arranged for inflation through a tubular stem 31 sealed at 32 to the panel 13 to provide a suitable conduit for gas passage between the interior of chamber 29 and the exterior of the trousers. Tube stem 31 has flexible walls and is provided with a pinch clip 33 to permit the tube to be closed to the passage of air or other suitable gas. A nipple 34 is provided on the end of tube stem 31 to enable it to be coupled to a tubulation 35 as by coupling 36.

A panel of heavy webbing 37 is maintained on the outer surface of the front abdominal section to prevent ballooning of that section. It is retained in place by straps 38 having cinching fasteners 39 such as conventional double D-rings secured to tabs 41. Straps 38 and tabs 41 are sewn into the side margins 42 and 43 of panel 13 and the strap are retained on webbing panel 37 by loops 44. When the trousers are applied to a patient the front abdominal panel 13 is secured to the rear abdominal panel 14 and straps 38 are cinched tight to draw the abdominal region about the patient prior to inflating chamber 29.

Leg subassemblies of the trousers of FIG. 1 are secured to the abdominal panels 13 and 14 as by a sewn seam 45. Each leg is formed into a single inflatable chamber 46 and 47. The right leg is formed by superimposing an outer panel 15 and 16 of the same or similar flexible, gas impervious fabric or sheet material of the abdominal region, on a coextensive inner panel 22 and 23 and sealing them along a marginal band 48. A similar sealing band 49 along the margins of the panels forming the left leg define chamber 47 between outer panels 17 and 18 and inner panels 24 and 25. Each leg is cut-away in the area of the crotch to provide a perineal cutout. Tube stems 52 and 53 with pinch clamps 54 and 55 provide gas conduits between the exterior of each leg and the chamber 46 and 47 respectively. As best seen in FIG. 7 individual leg chambers 46 and 47 extend across the inseam region 21 and around each leg. The outer side margins of the front and rear segments of each leg are joined by fasteners 56 and 57 which, advantageously, are double slide fasteners whereby portions of a leg or the abdominal region can be opened to release pressure on those regions or to permit access to those body portions of the patient for treatment.

The top of the abdominal region and bottom of the legs are finished with sewn seams 58, 59 and 61 and the slide. fasteners 56 and 57 are attached to the outer side margins of the abdominal region and the legs.

While any suitable source of pressurized gas can be employed to inflate the chambers 29, 46 and 47, a preferred emergency kit as might be employed for first aid utilizations of the anti-shock trousers is illustrated in FIG. 1. A carrying case 62 is arranged to contain trousers, a foot operated air pump 63, connecting hoses and a control and pressure monitoring console 64. Console 64 can be fitted into cover 65 of case 62 which can be separably coupled to the base of the case so that is can be placed next to the patient.

A tubulation or hose 66 extends from pump 63 to an input nipple 67 on console 64. Nipple 67 is in air flow communication by means of a manifold (not shown) with each of three output nipples 68, 69 and 71 through valves 72, 73 and 74 each having a "hold" or closed position, an "in" or inflate position for passing gas from input nipple 67 to their respective output nipples, and an "out" position for slowly bleeding gas from the respective ouput nipples, as to atmosphere. Color coding is employed identify the several sections of the trousers as by a border 75, 76 and 77 which can be matched with colored nuts or collars 78, 79 and 81 an the output nipples 68, 69 and 71 for the right leg, abdomen, and left leg respectively. Aneroid gauges 82, 83 and 84 within borders 75, 76 and 77 indicate pressures applied to the respective sections and are coupled to the respective output nipples 68, 69 and 71 as by suitable Ts (not shown) in the lines from the individual control valves to the output nipples. Gauges with a pressure range from 0-100 mm. of Hg are suitable although the chambers are usually pressurized to about 30 mm. of Hg.

Gas is fed from control console 64 to the inflatable chambers of the trousers through a hose assembly 82 including three tubes 83, 35 and 84 enclosed in a sheath 85. Color coding can be maintained to the garment by suitable collars 86, 87 and 88 on the console ends of the tubes and collars 89, 91 and 92 on the garment ends of the tubes to match borders 75, 76 and 77 and collars or nuts 78, 79 and 81. Further color coding can be provided at the input tubulations 52, 31 and 53 to the garment chambers 46, 29 and 47 by so coding collars 94, 93 and 95 on the tubulations of the respective right leg, abdomen and left leg chambers. Alternatively, tubes 83, 35 and 84 can be color coded in place of their end collars as can tube stems 52, 34, and 53.

In practice, the anti-shock trousers of FIGS. 1, 2 and 7 are applied where the victim has suffered an injury below the waist, to immobilize and splint fractures, to apply pressure to help control internal and external bleeding, and to administer a shock inhibiting auto transfusion by displacing blood flow to the lower torso and extremities, raising the blood pressure, and concentrating the victim's available blood flow in the upper body portions . The trousers are applied by positioning them as illustrated in FIG. 5 with the upper layer located in the area between where the patients legs would normally be. The patient is then placed on the trousers and the upper layer folded over the patient. The trousers are proportioned to avoid imposing pressure on the patient's rib cage while they are applied as high in the crotch area as comfort will permit. Where a double slide, slide fastener 56 and 57 are avialable and are at the bottom of the legs, they are both coupled to the free fastener stip and the upper slide is slid up each side to the waist. The abdominal belt is then cinched snugly to fit the patient.

With the trousers applied, the chambers which are appropriate to inflate in view of the patient's condition are inflated. The console 64 is placed adjacent the patient. Hose assembly 82 is attached to the tube stems 31, 52 and 53 and the output nipples 79, 78 and 81 in accordance with the proper color coded system and all hose clips 33, 54 and 55 are released. If all chambers are to be inflated, all air valves 73, 72 and 74 are turned to the "in" position and, assuming the foot pump 63 and its hose 66 are coupled through nipple 67, the foot pump is operated until the desired pressure is achieved, typically 20 to 25 m.m. of mercury.

The control console 64 lends itself to ease of selective inflation of the several chambers. If a section is not to be inflated initially, the valve for that section is set at the "hold" position, whereby no air will be passed from the pump to that section. Alternatively, if it is desired to relieve a section which has been inflated, its valve is turned to the "out" position and the air is bld from the section to atmosphere. Ordinarily, when pressure is relieved in a section it is opened at its fasteners 56 and 57. If the abdomen is not pressurized the upper slide fastener slides are lowered to seam 45. If a leg section is not pressurized its lower slide is raised to seam 45.

During inflation it may be desirable to inflate the sections to different degrees. This can be done by inflating all sections simultaneously to the lowest desired pressure. Then the valve of the section which is to be maintained at the low pressure is turned to "hold" and the remaining sections are raised in pressure by operating the pump. When all sections have reached their desired pressure, their respective valves should all be set at "hold." An overinflated section can be depressurized to the desired degree by bleeding air through the operation of the control valve to the "out" position while monitoring the drop in pressure on the gauge for the section.

Generally, it is desirable to maintain the established pressure in the trousers during transit of a patient and until a physician is present to take charge of the patient. If convenient, the control console 64 and pump 63 should remain connected to afford a means of making up any loss of pressure or altering the pressure if conditions dictate this procedure. However, the clips 33, 54 and 55 can be closed to hold pressure where separation of the trousers from the console 64 is required.

Alternative systems offering the treatment advantages set forth above are available. A three chambered device can be inflated to controlled pressurizations with a single control unit of the type illustrated in FIG. 3 which includes a single aneroid gauge 96 and a single control valve 97. In such a system the output hose 98 is provided with branches (not shown) which are connected to the several tube stems 31, 52 and 53 shown in FIG. 1 and control of pressure is either uniform for all chambers as indicated on gauge 96 or is selectively controlled by the tube clips 33, 54 and 55. Thus, if a chamber is not to be inflated clip is closed prior to operation of the foot pump. If a chamber is to be subject to a reduction in pressurization, the remaining chambers are closed by their tube clips and the control valve 97 and gauge 96 utilized to bleed air from the chamber while its pressure is monitored.

The embodiment of the anti-shock trousers pressure garment shown in FIGS. 3, 4 and 6 differs from that in FIGS. 1, 2 and 7 in that it is a two chamber garment which is operated effectively as a single chamber garment by a tubular interconnection between the chambers. Thus the trousers of FIG. 3 are made up of four panels of the flexible, gas impervious, fabric or sheet material, an outer front and rear panel 99 and 101 and an inner front and rear panel 102 and 103. The front panels 99 and 102 are joined along their peripheral margins as by a heat sealed or cement bonded band 104 to define a front air chamber 105, while the rear panels 101 and 103 are similarly bonded in the band 106 to from rear chamber 107. In this embodiment the bonded front and rear panels are joined along the inseam of each leg as at 108 as by a sewn seam outside the sealing bands 104 and 106. A slide fastener 109 provides means for separably joining the outer side margins of each side of the trousers. A perineal cutout 111 is provided above the inseam joint 108 in the crotch of the trousers and cinching panel 112 with straps 113 to the sides of the abdominal region of the front panels 99 and 102 are provided as in the case of the three chambered embodiment of FIG. 1.

While separate gas conduit tube stems 114 and 115 to the front and rear chambers 105 and 107 provide a means external of the garment to selectively inflate the chambers, in practice, it is usual to inflate both chambers simultaneously and therefore a T-coupling 116 joins tubes 114 and 115 to hose 98 from the control box 117. While no tube clips have been illustrated in FIG. 3 it is to be appreciated that they can provide on the individual tubulations 114 and 115 or on a length of tube on the leg of T 116. In the example the control box 117 provides a three-way control valve 97 having "in," "hold" and "out" positions as previously discussed to connect output nipple 118 either to pump 119 via hose 121, to cut off flow from the garment through nipple 118 or to bleed air to atmosphere from the garment. Guage 96 is connected downstream of valve 97 and ahead of nipple 118 to afford continuous monitoring of pressure in the chambers 105 and 107.

A second tube stem 122 can be provided in the outer panel 99 of front chamber 105 to receive an aneroid guage coupling to enable air pressure in the trousers to be measured if not control box 117 is available. An aneroid gauge (not shown) can be clipped or secured to the cinch belt in such an arrangement.

As in the embodiment of FIG. 1 the anti-shock trousers unit of FIG. 3 has a protective carrying case 123 for the garment, hoses, pump and control box.

It is to be appreciated that many varients of the constuction and materials employed in the preferred embodiment are within the concepts of this invention. For example, cast sheet material which is flexible and gas impervious can be substituted for woven material in forming the inflatable chambers. The chambers need not be integral with the casing of the garment but could be in pockets within the garment or constrained by a suitable flexible and compliant structure fitted to the patient in the manner disclosed. Other forms of valving and gas conduits can be employed. Various forms of fasteners other than zippers are available provided they provide relatively uniform distribution of closure constraint over the effective area of the garment. The accessories providing a source of pressurized gas, control of gas flow, and monitoring of the gas pressure within the chambers can be of types and forms other than those shown. Accordingly, it is to be understood that this detailed disclosure is to be read as exemplary and not in a limiting sense.

What is claimed is:

1. A pressure garment comprising a front face panel and a rear face panel of flexible fabric; an abdominal region on each of said front and rear panels adapted to cover a portion of the abdomen of a patient; a pair of leg regions on each of said front and rear panels adapted to cover a portion of respective legs of a patient, said leg regions of each panel being dependent from and integral with said abdominal region of said panel; a permanent junction between said front and rear panels along the inseam portion of each leg; said front and rear panels being separate along outer side margins of said abdominal region and said leg regions; fastener means along each outer side margin of said abdominal and leg regions for separably securing said front and rear panels together along said outer side margins; a gas chamber of flexible gas impervious fabric between said front and rear panels and extending over a preponderance of the area of at least one of said regions of at least one panel; and a gas conduit in gas flow communication between the exterior of said garment and said chamber.

2. A pressure garment according to claim 1 wherein said gas chamber extends over a preponderance of the abdominal region of said front panel; and including cinching means extending across the outer side of said abdominal region of said front panel between the outer side margins of said front panel abdominal region to inhibit ballooning of said region upon inflation of said chamber.

3. A pressure garment according to claim 1 wherein said gas chamber extends over a preponderance of the abdominal region and both legs of at least one panel of said garment.

4. A pressure garment according to claim 3 wherein said gas chamber is adjacent said front panel; and including cinching means extending across the outer side of said abdominal region of said front panel between the outer side margins of said front panel abdominal region to inhibit ballooning of said region upon inflation of said chamber.

5. A pressure garment according to claim 1 wherein a first gas chamber extends over a preponderance of the front panel and a second gas chamber extends over a preponderance of the rear panel; and wherein first and second gas conduits communicate between the exterior of said garment and said first and second chambers respectively.

6. A pressure garment according to claim 1 wherein a first gas chamber extends over a preponderance of the abdominal region of said front panel, a second gas chamber extends over a preponderance of one leg region of said front and rear panels and said respective inseam region, and a third gas chamber extends over a preponderance of the other leg region of said front and rear panels and said respective inseam region; and wherein first, second and third gas conduits communicate between the exterior of said garment and said first second and third chambers respectively.

7. A pressure garment according to claim 1 wherein said fastener means are slide fasteners.

8. A pressure garment according to claim 6 wherein said fastener means are selectively operable in part and in their entirety along said side margins.

9. A pressure garment according to claim 8 wherein said fastener means are double ended slide fasteners.

10. A pressure garment according to claim 2 wherein said cinching means comprises a panel of stiff webbing of a height of the order of the height of said abdominal region and a width of the order of the height, a plurality of straps secured to and extending from the sides across the width of said abdominal region of the front panels, and a fastening means for said straps secured to opposite sides of said abdominal region of the front panel.

11. A pressure garment according to claim 1 including means selectively to introduce gas under pressure into said chamber through said conduit.

12. A pressure garment according to claim 11 including an aneroid gauge coupled to said garment to indicate the gas pressure within said chamber.

13. A pressure garment according to claim 12 including a manually operative slow release valve for releasing gas from said chamber to reduce the gas pressure therein.

14. A pressure garment comprising a front panel and a rear panel of flexible, gas impervious fabric adapted to cooperatively envelope the lower abdomen of a patient; an abdominal panel of flexible, gas impervious fabric generally coextensive with and in registry with said front panel; a marginal seal between said abdominal panel and said registering front panel to form a first gas chamber between said abdominal panel and said front panel; separate outer leg panels of flexible, gas impervious fabric each depending from both said front and rear panels and each adapted to extend across the inner faces of and envelope the respective legs of a patient; separate inner leg panels of flexible, gas impervious fabric generally coextensive with and in registry with each of said outer leg panels; a marginal seal between respective inner and outer leg panels to form individual gas chambers adapted to envelope the respective legs of a patient; a stiff panel extending over a substantial portion of the width and height of said first chamber and generally conformable to the abdominal contour of the patient; a plurality of straps of adjustable length extending across said front panel and secured to opposed side margins of said panel; means to maintain said stiff panel on said front panel beneath said straps; gas conduits communicating between the exterior of said garment and each of said first and leg enveloping gas chambers; flexible walled tubulations coupled to each of said gas conduits; valve means for each tubulation to open and close said tubulations for gas flow; a source of pressurized gas coupled to said tubulations; a control valve intermediate said source and said tubulations for selectively coupling said tubulations to said source and to atmosphere; and pressure guage coupled to said tubulations.

15. A pressure garment according to claim 14 including individual control valves intermediate said source and each of a plurality of said tubulations for individually selectively coupling said tubulations to said source and to atmosphere; and individual pressure gauges coupled between said individual control valves and said tubulations.

16. A pressure garment according to claim 15 wherein said source of gas, control valves, and pressure gauges are separable from said gas conduits and wherein said tubulations and said control valves and pressure gauges are color coded to facilitate association of said elements in their assembly and operation for control and monitoring of gas pressures in said respective chambers.

* * * * *